(12) United States Patent
Denson et al.

(10) Patent No.: US 11,684,277 B2
(45) Date of Patent: Jun. 27, 2023

(54) MONITORING VITAL PARAMETERS OF A COMPRESSION GARMENT WEARER

(71) Applicant: KPR U.S., LLC, Mansfield, MA (US)

(72) Inventors: Jesse Denson, Lincoln, RI (US); Laura Keith, Acton, MA (US); Scott Wudyka, Marlboro, MA (US); Zaheer Abdool, Randolph, MA (US)

(73) Assignee: KPR U.S., LLC, Mansfield, MA (US)

( * ) Notice: Subject to any disclaimer, the term of this patent is extended or adjusted under 35 U.S.C. 154(b) by 214 days.

(21) Appl. No.: 16/021,199

(22) Filed: Jun. 28, 2018

(65) Prior Publication Data

US 2019/0000329 A1    Jan. 3, 2019

Related U.S. Application Data

(60) Provisional application No. 62/527,155, filed on Jun. 30, 2017.

(51) Int. Cl.
*A61B 5/022* (2006.01)
*A61B 5/025* (2006.01)
(Continued)

(52) U.S. Cl.
CPC .......... *A61B 5/02225* (2013.01); *A41D 1/005* (2013.01); *A61B 5/0205* (2013.01); *A61B 5/02438* (2013.01); *A61B 5/7246* (2013.01); *A61H 9/0078* (2013.01); *A61H 9/0092* (2013.01); *A61B 5/02455* (2013.01); *A61B 5/0816* (2013.01); *A61B 5/4833* (2013.01); *A61B 5/6828* (2013.01);
(Continued)

(58) Field of Classification Search
CPC .............. A61B 5/02225; A61B 5/0205; A61B 5/02438; A61B 5/7246; A61B 17/1355; A61B 5/02455; A61B 5/0816; A61B 5/4833; A61B 5/6828; A61B 5/6829; A61B 5/6843; A61B 5/7207; A61B 5/725; A61H 9/0078; A61H 9/0092; A61H 2201/5007; A61H 2230/30; A61H 2230/04; A61H 2201/5038; A61H 2201/5035; A61H 2205/10; A61H 2201/1238; A61H 2201/5071; A61H 2230/25; A61H 2201/501; A61H 2201/165; A41D 1/005
See application file for complete search history.

(56) References Cited

U.S. PATENT DOCUMENTS 4,461,266 A    7/1984   Hood, Jr. et al.
4,543,962 A   10/1985   Medero et al.
(Continued)

FOREIGN PATENT DOCUMENTS

JP    2004-065725 A    3/2004
JP    2005348903 A    12/2005
(Continued)

*Primary Examiner* — Nathan J Jenness
*Assistant Examiner* — Justin Xu
(74) *Attorney, Agent, or Firm* — ArentFox Schiff LLP

(57) ABSTRACT

Monitoring vital parameters of a wearer of a compression garment by analyzing a pressure signal waveform indicative of a fluid pressure in an inflatable and deflatable bladder of the compression garment. Analyzing the pressure signal waveform for an oscillating amplitude as a function of time and/or a representation of a pulse of the wearer provides an indication of blood pressure of the wearer.

21 Claims, 8 Drawing Sheets

(51) Int. Cl.
    *A61B 5/00*     (2006.01)
    *A61H 9/00*     (2006.01)
    *A61B 17/135*     (2006.01)
    *A41D 1/00*     (2018.01)
    *A61B 5/0205*     (2006.01)
    *A61B 5/024*     (2006.01)
    *A61B 5/0245*     (2006.01)
    *A61B 5/08*     (2006.01)

(52) U.S. Cl.
    CPC .......... *A61B 5/6829* (2013.01); *A61B 5/6843* (2013.01); *A61B 5/725* (2013.01); *A61B 5/7207* (2013.01); *A61B 17/1355* (2013.01); *A61H 2201/1238* (2013.01); *A61H 2201/165* (2013.01); *A61H 2201/501* (2013.01); *A61H 2201/5007* (2013.01); *A61H 2201/5035* (2013.01); *A61H 2201/5038* (2013.01); *A61H 2201/5071* (2013.01); *A61H 2205/10* (2013.01); *A61H 2230/04* (2013.01); *A61H 2230/25* (2013.01); *A61H 2230/30* (2013.01)

(56) References Cited

U.S. PATENT DOCUMENTS

| | | | |
|---|---|---|---|
| 4,718,427 A | 1/1988 | Russell | |
| 2001/0000262 A1* | 4/2001 | McEwen | A61H 9/0078 601/11 |
| 2003/0069507 A1 | 4/2003 | Nishibayashi | |
| 2004/0181157 A1* | 9/2004 | Medero | A61B 5/02225 600/500 |
| 2005/0187500 A1* | 8/2005 | Perry | A61H 9/0078 601/152 |
| 2006/0155196 A1* | 7/2006 | Ramsey | A61B 5/02141 600/490 |
| 2008/0033307 A1* | 2/2008 | Baudoin | A61H 9/0092 600/490 |
| 2009/0118628 A1* | 5/2009 | Zhou | A61B 5/1075 600/499 |
| 2010/0324429 A1 | 12/2010 | Leschinsky | |
| 2011/0066044 A1* | 3/2011 | Moon | A61B 5/02125 600/485 |
| 2014/0366874 A1* | 12/2014 | Deutsch | A61M 16/044 128/202.13 |
| 2016/0198959 A1* | 7/2016 | Qasem | A61B 5/7225 600/493 |

FOREIGN PATENT DOCUMENTS

| | | |
|---|---|---|
| JP | 2016-064125 A | 4/2016 |
| KR | 20120120262 A | 11/2012 |
| WO | 02055007 A2 | 7/2002 |

* cited by examiner

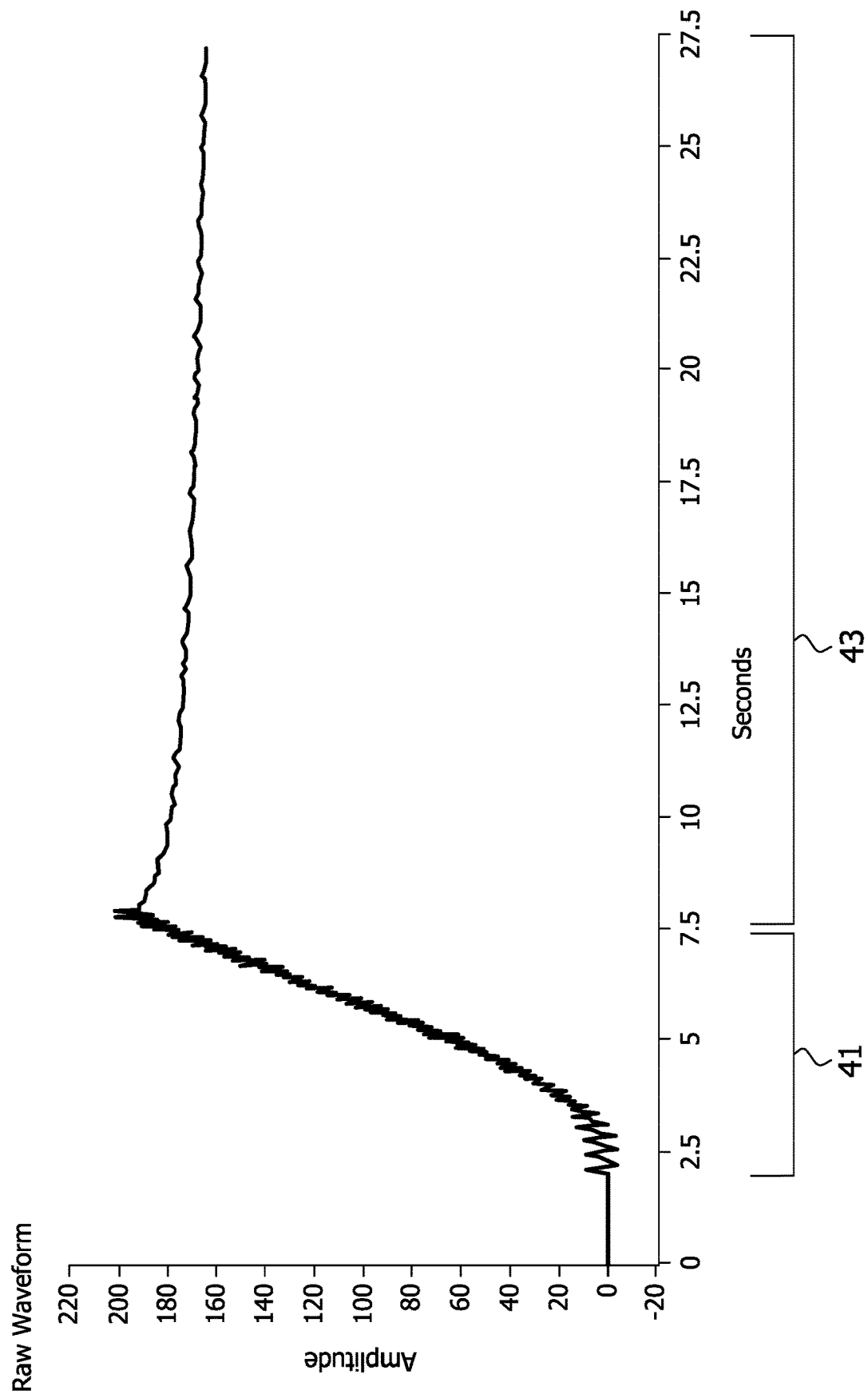

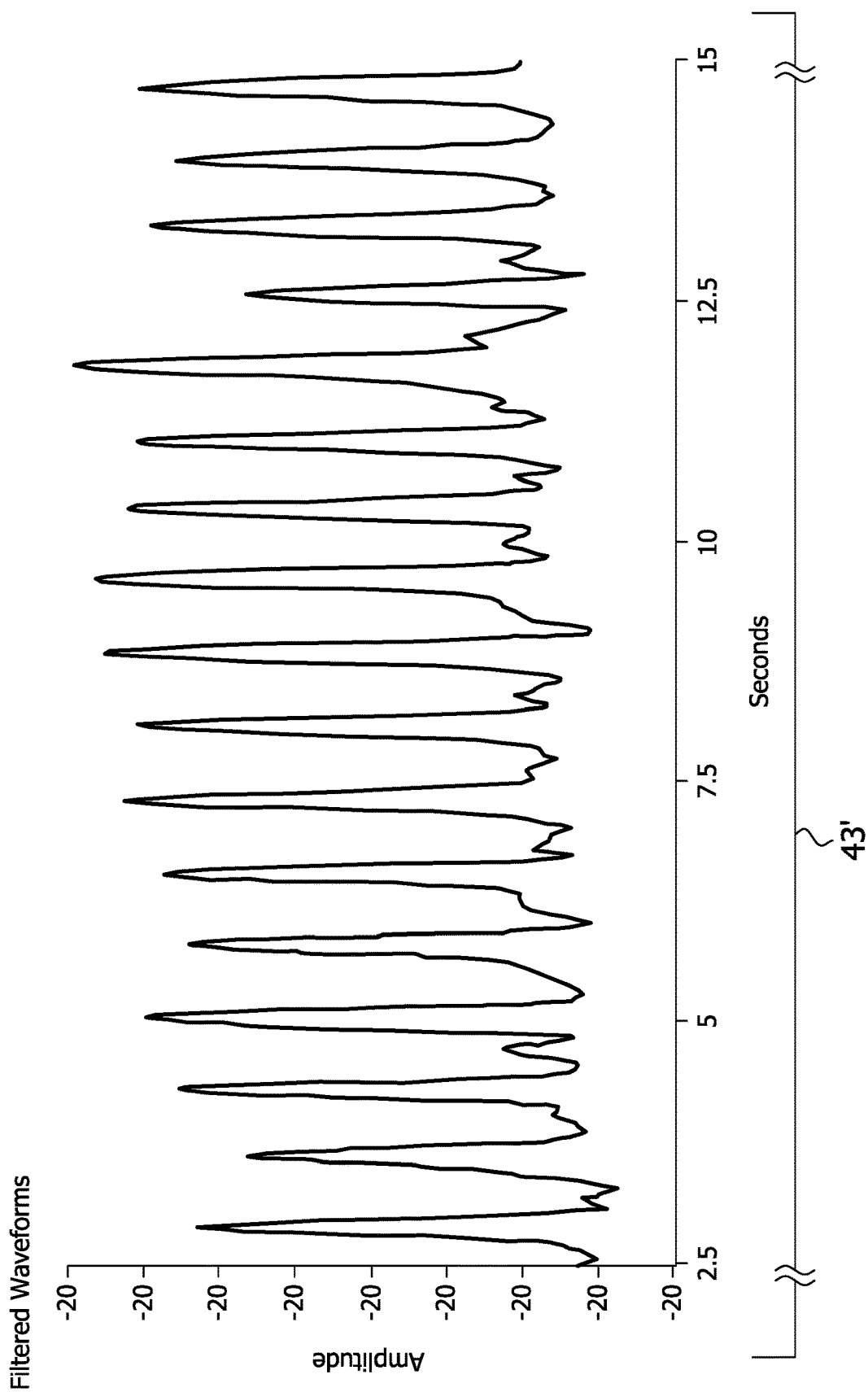

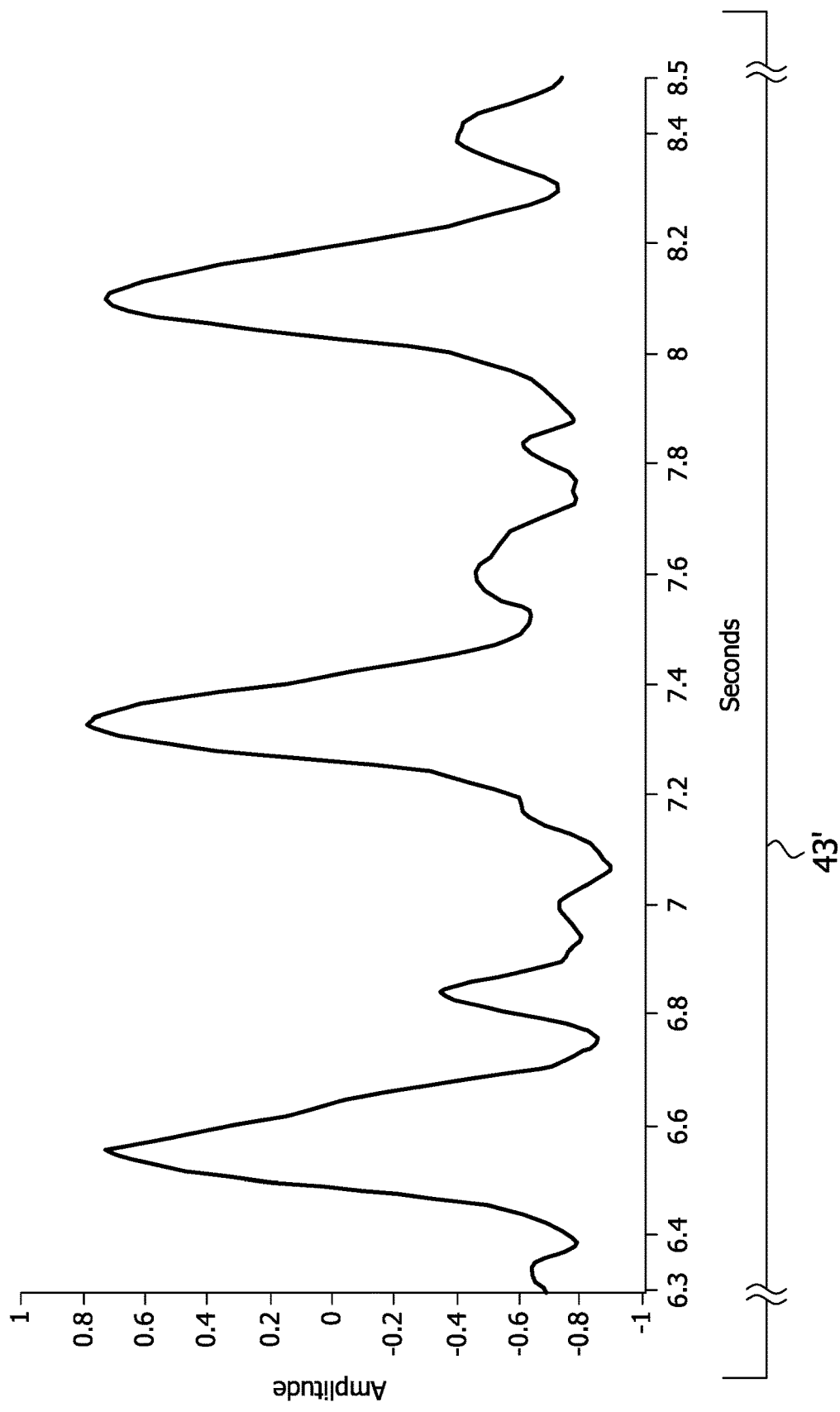

MONITORING VITAL PARAMETERS OF A COMPRESSION GARMENT WEARER

CROSS-REFERENCE TO RELATED APPLICATIONS

This application claims priority from U.S. Provisional Patent Application Ser. No. 62/527,155, filed Jun. 30, 2017, the disclosure of which is incorporated in its entirety by reference, including the contents and teachings of any references contained therein.

BACKGROUND

Intermittent pneumatic compression (IPC) systems include devices used to apply pressurized fluid, such as air, to a limb of a patient or wearer. In some instances, pressurized air is applied to the lower limb of a patient at risk for the formation of a blood clot (thrombus) associated with deep vein thrombosis (DVT). An IPC system typically includes a pumping unit to manage pressurization of the fluid, a tubing set to extend the delivery of fluid beyond the pumping unit, and a compression garment which is wrapped around the patient's limb and contains the pressurized fluid. The IPC system intermittently pressurizes the garment to apply therapeutic compression to the patient's limb, moving blood from that area of the limb. Many IPC systems utilize a pressure sensor as the sole means of feedback. The pressure sensor output is used to adjust fluid delivery to the compression garment and maintain prescribed pressures, but the measurable pressure is confined to the pressure within the compression garment and tubing.

SUMMARY

The present disclosure is directed to systems and methods of determining a blood pressure and/or a pulse rate of a compression garment wearer.

In one aspect, a controller for controlling inflation and deflation of at least one bladder of a garment to provide compression therapy treatment to a wearer of the garment includes a memory, one or more processors, and a non-transitory, computer-readable storage medium. The non-transitory, computer-readable storage medium includes computer-executable instructions for causing the one or more processors to receive, from a pressure sensor, a signal indicative of fluid pressure in the at least one bladder of the garment and determine whether the received signal includes oscillating amplitude as a function of time. The non-transitory, computer-readable storage medium also includes computer-executable instructions for causing the one or more processors to estimate a blood pressure of the wearer of the garment based at least in part on the determination of whether the received signal includes oscillating amplitude as a function of time.

In another aspect, a system includes a compression garment including at least one inflatable and deflatable bladder and the compression garment is securable about a limb of a wearer. The system further includes a controller for controlling inflation and deflation of at least one bladder of a garment to provide compression therapy treatment to a wearer of the garment. The controller includes a memory, one or more processors, and a non-transitory, computer-readable storage medium that includes instructions for causing the one or more processors to receive, from a pressure sensor, a signal indicative of fluid pressure in the at least one bladder of the garment and determine whether the received signal includes oscillating amplitude as a function of time. The non-transitory, computer-readable storage medium also includes computer-executable instructions for causing the one or more processors to estimate the blood pressure of the wearer of the garment based at least in part on the determination of whether the received signal includes oscillating amplitude as a function of time.

In another aspect, a controller for controlling inflation and deflation of at least one bladder of a garment to provide compression therapy treatment to a wearer of the garment includes a memory, one or more processors, and a non-transitory, computer-readable storage medium. The non-transitory, computer-readable storage medium includes computer-executable instructions for causing the one or more processors to receive, from a pressure sensor, a signal indicative of fluid pressure in the at least one bladder of the garment, and determine whether the received signal includes a representation of a pulse of the wearer. The non-transitory, computer-readable storage medium also includes computer-executable instructions for causing the one or more processors to determine a blood pressure of the wearer of the garment based at least in part on the determination of whether the received signal includes a signal indicative of the pulse of the wearer.

In another aspect, a system includes a compression garment including at least one inflatable and deflatable bladder and the compression garment is securable about a limb of a wearer. The system further includes a controller for controlling inflation and deflation of at least one bladder of a garment to provide compression therapy treatment to a wearer of the garment. The controller includes a memory, one or more processors, and a non-transitory, computer-readable storage medium that includes instructions for causing the one or more processors to receive, from a pressure sensor, a signal indicative of fluid pressure in the at least one bladder of the garment, and determine whether the received signal includes a representation of a pulse of the wearer. The non-transitory, computer-readable storage medium also includes computer-executable instructions for causing the one or more processors to determine a blood pressure of the wearer of the garment based at least in part on the determination of whether the received signal includes a signal indicative of the pulse of the wearer.

Embodiments can include one or more of the following advantages.

In some embodiments, a determination of a blood pressure of a wearer is performed using a signal indicative of pressure in an inflatable bladder of the compression garment during a static period, providing a real-time and automated indication of the blood pressure of a wearer. As compared to observations of multiple medical devices made by a caregiver, the real-time and automated indication of blood pressure of the wearer described herein can provide for a more accurate blood pressure measurement, a more accurate indication of patient compliance with treatment protocols, and/or can reduce the burden on the caregiver with respect to monitoring patient vital parameters. As compared to monitoring vital parameters of a wearer who is receiving treatment, the indication of blood pressure of the wearer described herein can provide for monitoring of wearer vital parameters with minimal equipment and enhanced comfort.

Other aspects, features, and advantages will be apparent from the description and drawings, and from the claims.

BRIEF DESCRIPTION OF THE DRAWINGS

FIGS. 4A-4D are graphical representations of a pressure profile produced by the compression system of FIG. 1 when a compression garment of the system is in a wrapped configuration on a limb of a wearer.

DETAILED DESCRIPTION

As used herein, the terms "proximal" and "distal" represent relative locations of components, parts and the like of a compression garment when the garment is worn. For example, a "proximal" component is disposed most adjacent to the wearer's torso, a "distal" component is disposed most distant from the wearer's torso, and an "intermediate" component is disposed generally anywhere between the proximal and distal components. Further, as used herein, the terms "wrapped" and "unwrapped" define conditions of the garment where the garment is properly applied to the wearer's limb (e.g., wrapped, worn, etc.) and where the garment is removed from the wearer's limb (e.g., unwrapped, unworn, etc.).

Aspects of the disclosure herein are related to U.S. patent application Ser. No. 15/290,026, filed Oct. 11, 2016 and PCT application number PCT/US2016/056296, filed on Oct. 10, 2016, and the applications from which they claim priority: U.S. Provisional Patent Application Ser. Nos. 62/239,527, 62/239,493, and 62/239,566, all filed Oct. 9, 2015, and U.S. Provisional Patent Application Ser. No. 62/329,233, filed Apr. 29, 2016. The entire contents of the above-identified applications are expressly incorporated herein by reference, including the contents and teachings of any references contained therein.

Figure 1:
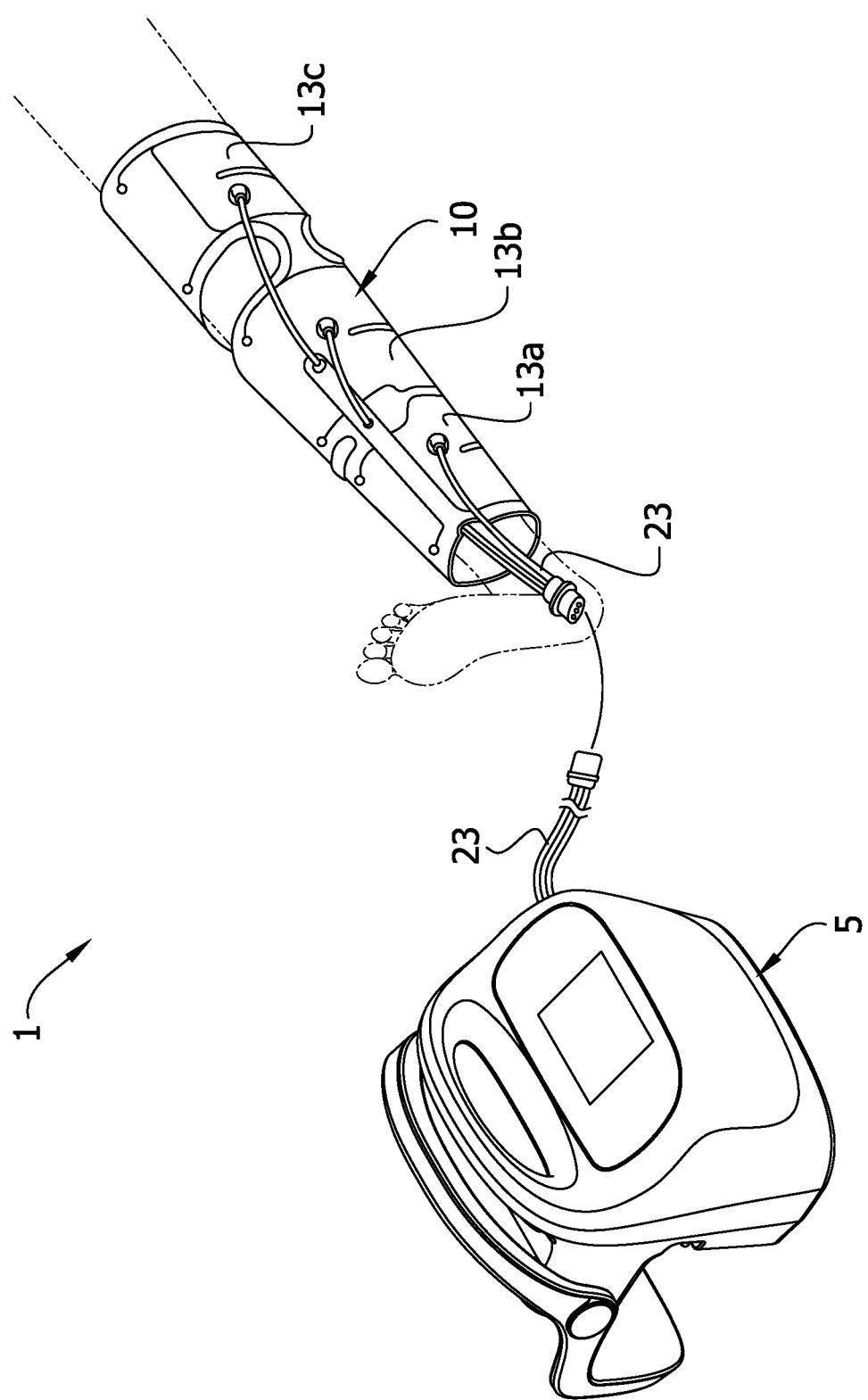
FIG. 1 is a perspective of a compression system including a compression garment and a controller.
Figure 2:
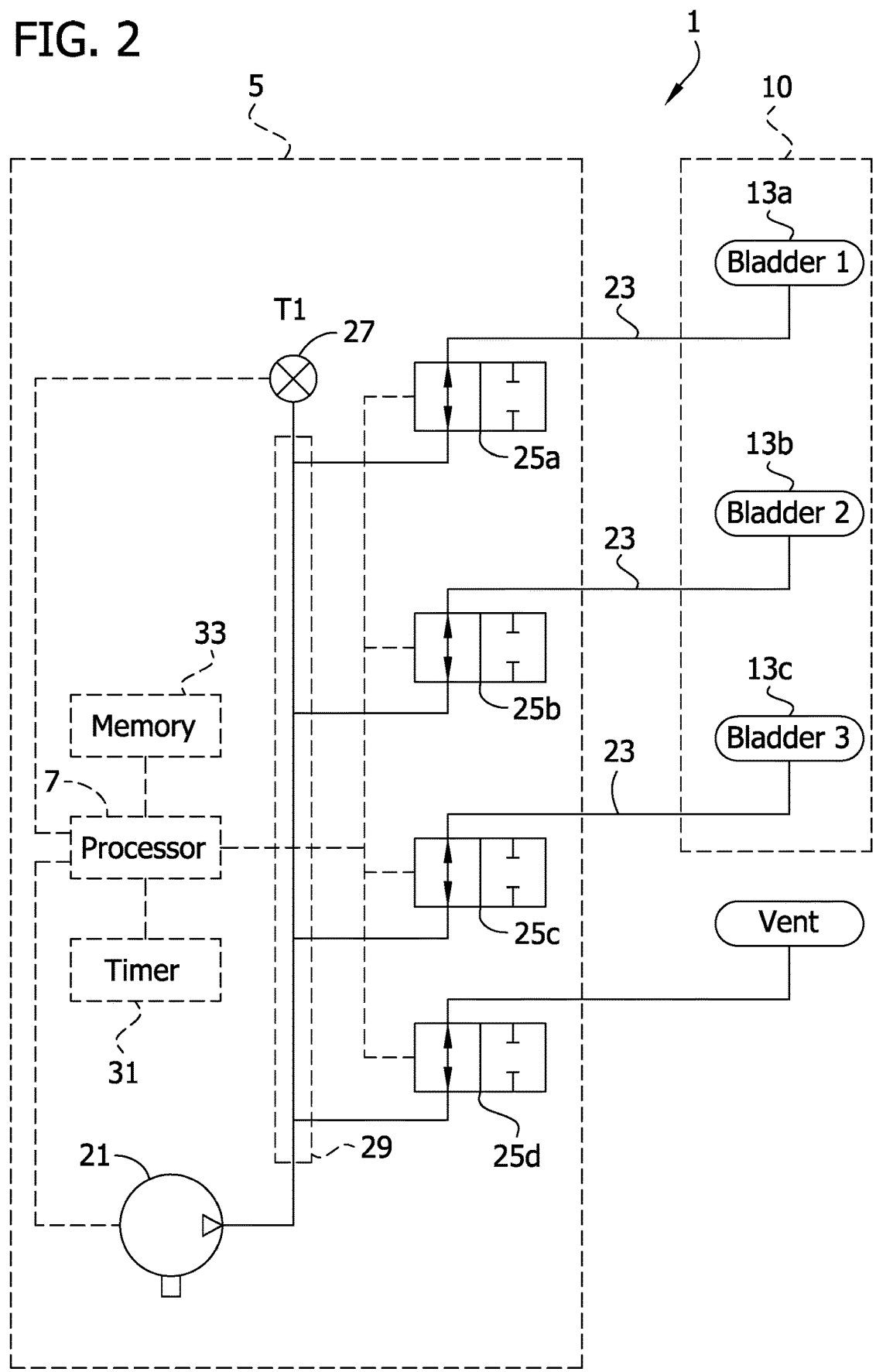
FIG. 2 is a schematic of an exemplary compression system of FIG. 1, including a schematic of a pneumatic circuit.

Referring to FIGS. 1 and 2, a compression system 1 includes a compression garment 10 for applying sequential compression therapy to a limb or limbs of a wearer and a controller 5 having one or more processors 7 and computer executable instructions embodied on a non-transitory computer readable storage medium (e.g., memory) 33. The computer executable instructions include instructions for causing the one or more processors 7 to control operation of the compression system 1. The compression garment 10 includes a distal inflatable bladder 13a, an intermediate inflatable bladder 13b, and a proximal inflatable bladder 13c. The compression garment 10 can be fastened around the wearer's limb and, in some embodiments, is adjustable to fit limbs of different circumferences. The inflatable bladders 13a, 13b, 13c, in some embodiments, extend at least partially around a portion of the wearer's limb. For example, inflatable bladders 13a, 13b, 13c may be posterior-only bladders.

As described in further detail below, the controller 5 determines, based at least in part on a measured pressure of one or more of the inflatable bladders 13a, 13b, 13c, a blood pressure and/or a pulse rate of a wearer around whose limb the compression garment 10 is applied (i.e., in a wrapped configuration around) and, in some embodiments, correlates the blood pressure with an arterial blood pressure and provides an indication of the determined blood pressure and/or correlated arterial blood pressure (e.g., by providing an audible alarm and/or by providing a visual indication on a graphical user interface). In additional or alternative embodiments, the controller 5 determines, based at least in part on the measured pressure of one or more of the inflatable bladders 13a, 13b, 13c, a respiration rate of the wearer, changes in peripheral resistance (e.g., due to vaso-dilating/constricting drugs, etc.), and/or motions of the wearer (e.g., monitoring patient motion). As also described in further detail below, the controller 5 can control operation of the compression system 1 to perform an inflation cycle, in which the inflatable bladders 13a, 13b, 13c are inflated to apply pressure to the wearer's limb to establish, for example, a gradient pressure applied to the wearer's limb by inflatable bladders 13a, 13b, 13c of the compression garment 10 during one or more compression cycles. As also described in further detail below, each therapeutic compression cycle can include an inflation phase for each of the bladders 13a, 13b, 13c, a decay phase for each of the bladders 13a and 13b, and a decompression or vent phase for each of the bladders 13a, 13b, 13c. The end-of-cycle pressure of each bladder 13a, 13b, 13c is the pressure in each bladder 13a, 13b, 13c prior to initiation of the decompression phase of the respective bladder 13a, 13b, 13c.

The compression garment 10 is a thigh-length sleeve positionable around the leg of the wearer, with the distal bladder 13a around the wearer's ankle, the intermediate bladder 13b around the wearer's calf, and the proximal bladder 13c around the wearer's thigh. The inflatable bladders 13a, 13b, 13c expand and contract under the influence of fluid (e.g., air or other fluids) delivered from a pressurized fluid source 21 (e.g., a pump or compressor) in electrical communication with the controller 5. The pressurized fluid source 21 delivers pressurized fluid (e.g., air) to the inflatable bladders 13a, 13b, 13c through tubing 23.

Referring to FIG. 2, each inflatable bladder 13a, 13b, 13c is in fluid communication with a respective valve 25a, 25b, 25c. A pressure sensor 27 is in communication (e.g., fluid communication and/or mechanical communication) with a manifold 29 to measure a signal indicative of pressure in the manifold 29. Fluid communication between the manifold 29 and the respective inflatable bladders 13a, 13b, 13c can be controlled through control of the position of the respective valves 25a, 25b, 25c (e.g., through activation and/or deactivation of the respective valves 25a, 25b, 25c). The pressure sensor 27 is in electrical communication with the processor 7 such that the processor 7 receives, from the pressure sensor 27, signals indicative of the pressure of the manifold 29 and/or one or more of the inflatable bladders 13a, 13b, 13c in fluid communication with the manifold 29 as a result of the positions of the respective valves 25a, 25b, 25c. If only one bladder 13a, 13b, or 13c is in fluid communication with the manifold 29, the signal received from the pressure sensor 27 is indicative of the pressure of the respective bladder 13a, 13b, 13c in fluid communication with the manifold 29. For example, the pressure sensor 27 provides a signal indicative of the pressure in the inflatable bladder 13a when valve 25a is open and valves 25b, 25c are closed. Similarly, the pressure sensor 27 provides a signal indicative of the pressure in the bladder 13b when the valve 25b is open and the valves 25a and 25c are closed. Likewise, the pressure sensor 27 provides a signal indicative of the pressure in the inflatable bladder 13c when the valve 25c is open and the valves 25a and 25b are closed. A vent valve 25d is actuatable to control fluid communication between the manifold 29 and a vent port, which vents to ambient atmosphere. All bladders 13a, 13b, 13c can be vented using the vent valve 25d.

Each valve 25a, 25b, 25c is a 2-way/2-position, normally open, solenoid valve. Each valve 25a, 25b, 25c includes two ports and is actuatable to place an inlet port in fluid communication with a bladder port in a first, open position. Each valve 25a, 25b, 25c is further actuatable to shut off fluid communication between the inlet port and the bladder port. The inlet port of each valve 25a, 25b, 25c is in fluid communication with the pressurized fluid source 21 and the manifold 29. The bladder port of each valve 25a, 25b, 25c is in fluid communication with a respective inflatable bladder 13a, 13b, 13c.

Any one of the bladders 13a, 13b, 13c can be placed in fluid communication with the pressurized fluid source 21 and the manifold 29 by the respective valve 25a, 25b, 25c to deliver pressurized fluid to the bladder 13a, 13b, 13c. After the bladder 13a, 13b, 13c is inflated, the respective valve 25a, 25b, 25c can be closed to hold the fluid in the respective bladder 13a, 13b, 13c. Thus, the bladders 13a, 13b, 13c of the compression garment 10 can be individually inflated by opening the respective valve 25a, 25b, 25c and closing the other valves 25a, 25b, 25c so that only the one bladder 13a, 13b, 13c associated with the opened valve 25a, 25b, 25c is in fluid communication with the pressurized fluid source 21 and the manifold 29.

The vent valve 25d is also a 2-way/2-position, normally open, solenoid valve. The vent valve 25d includes two ports and is actuatable to place an inlet port in fluid communication with a vent port in a first position. The vent inlet port is in fluid communication with a vent port in a first position. The vent valve 25d is further actuatable to shut off fluid communication between the inlet port and the vent port. The inlet port of vent valve 25d is in fluid communication with the pressurized fluid source 21 and the manifold 29. The vent port of the vent valve 25d is in fluid communication with ambient atmosphere.

It should be appreciated that the valves 25a, 25b, 25c, 25d of FIG. 2 could be other types and have other arrangements within the compression system 1 without departing from the scope of the present disclosure. For example, referring to FIG. 3, the valves may be valves 35a, 35b, 35c, which are 3-way/2-position solenoid valves and are actuatable to control the pressure in bladders 13a, 13b, 13c without a vent valve.

With reference again to FIG. 2, the computer executable instructions embodied on the non-transitory, computer readable storage medium 33 can include instructions to cause the one or more processors 7 to pressurize (e.g., inflate) the inflatable bladders 13a, 13b, 13c to provide cyclical therapeutic compression pressure to a wearer's limb. For example, the computer executable instructions embodied on the non-transitory, computer readable storage medium 33 can include instructions to cause the one or more processors 7 to control the pressurized fluid source 21 and/or the valves 25a, 25b, 25c, 25d to pressurize the inflatable bladders 13a, 13b, 13c to therapeutic compression pressures for a predetermined amount of time to move the blood in the limb from regions underlying the inflatable bladders 13a, 13b, 13c. For example, the one or more processors 7 can use timing signals and/or timing data provided by the timer 31 to measure the amount of time the inflatable bladders 13a, 13b, 13c are pressurized. In accordance with one or more embodiments, the timer 31 can be comprised of a clock, one or more timer circuits (e.g., 555 timer integrated circuits, etc.), computer executable instructions that comprise timing routines, and/or other timers familiar to those skilled in the art. The length of time the bladder 13a, 13b, 13c is held at the compression pressure is referred to herein as a decay phase. Following the decay phase is a decompression phase. The computer executable instructions include instructions to cause the one or more processors 7 to control the pressurized fluid source 21 and/or the valves 25a, 25b, 25c, 25d to reduce the pressure in the inflatable bladders 13a, 13b, 13c to a lower pressure (e.g., atmospheric pressure).

The compression system 1 can determine a blood pressure, a pulse rate, a respiration rate, changes in peripheral resistance, and/or motions of a wearer around whose limb the compression garment 10 is applied (i.e., in a wrapped configuration around) and, in certain embodiments, can provide an indication of that determination, which can facilitate, for example, monitoring the wearer's vital parameters with compression garment 10 and tracking the wearer's compliance with a prescribed therapeutic use of the compression garment 10. For example, monitoring vital parameters via compression garment 10 reduces the negative impact to wearer comfort that would result from utilizing a sphygmomanometer or the like in addition to compression garment 10. Moreover, monitoring vital parameters via compression garment 10 reduces the need for healthcare professionals (e.g., nurses) to monitor multiple medical devices which reduces the potential for missed information and/or errors. The computer executable instructions embodied on the non-transitory, computer readable storage medium 33 include instructions to cause the one or more processors 7 to analyze pressure signal data received from the pressure sensor 27 during a static period of a therapeutic cycle of the compression system 1. The computer executable instructions embodied on the non-transitory, computer readable storage medium 33 include instructions to cause the one or more processors 7 to detect waveform peaks in the output of pressure sensor 27 correlated to a heartbeat range of the wearer, determine a frequency of the waveform peaks, and assess the oscillation amplitude for blood pressure estimation. The computer executable instructions embodied on the non-transitory, computer readable storage medium 33 include instructions to cause the one or more processors 7 to, based on magnitude of the oscillating amplitude, utilize one or more algorithms to estimate a blood pressure of the wearer around whose limb the compression garment 10 is applied. The computer executable instructions embodied on the non-transitory, computer readable storage medium 33 include instructions to cause the one or more processors 7 to correlate the estimated blood pressure of the wearer based on magnitude of the oscillating amplitude with a corresponding arterial blood pressure of the wearer around whose limb the compression garment 10 is applied.

In an exemplary embodiment, the computer executable instructions cause the one or more processors 7 to receive pressure signal data from the pressure sensor 27. The computer executable instructions can include instructions to cause the one or more processors 7 to process a single waveform representative of the pressures within one or more of the bladders 13a, 13b, 13c. It should be appreciated that the one or more processors 7 may process multiple waveforms without departing from the scope of the present disclosure. By monitoring the pressure signals and corresponding pressure data during, for example, a static period of the therapy cycle, the one or more processors 7 can detect certain characteristics on the waveform that are indicative of a heartbeat of the wearer. In certain embodiments, during the static period, the pressure sensor 27 remains (or is intentionally placed) in constant communication (e.g., fluidic and/or mechanical communication) with one or more of the bladders 13a, 13b, 13c. Exemplary static periods include non-therapeutic cycles (e.g., pressures in bladders 13a, 13b, 13c of less than about 25 mmHg), a subset of an initial garment detection period, an extension of a therapy cycle, and/or a venous refill measurement period.

Figure 3:
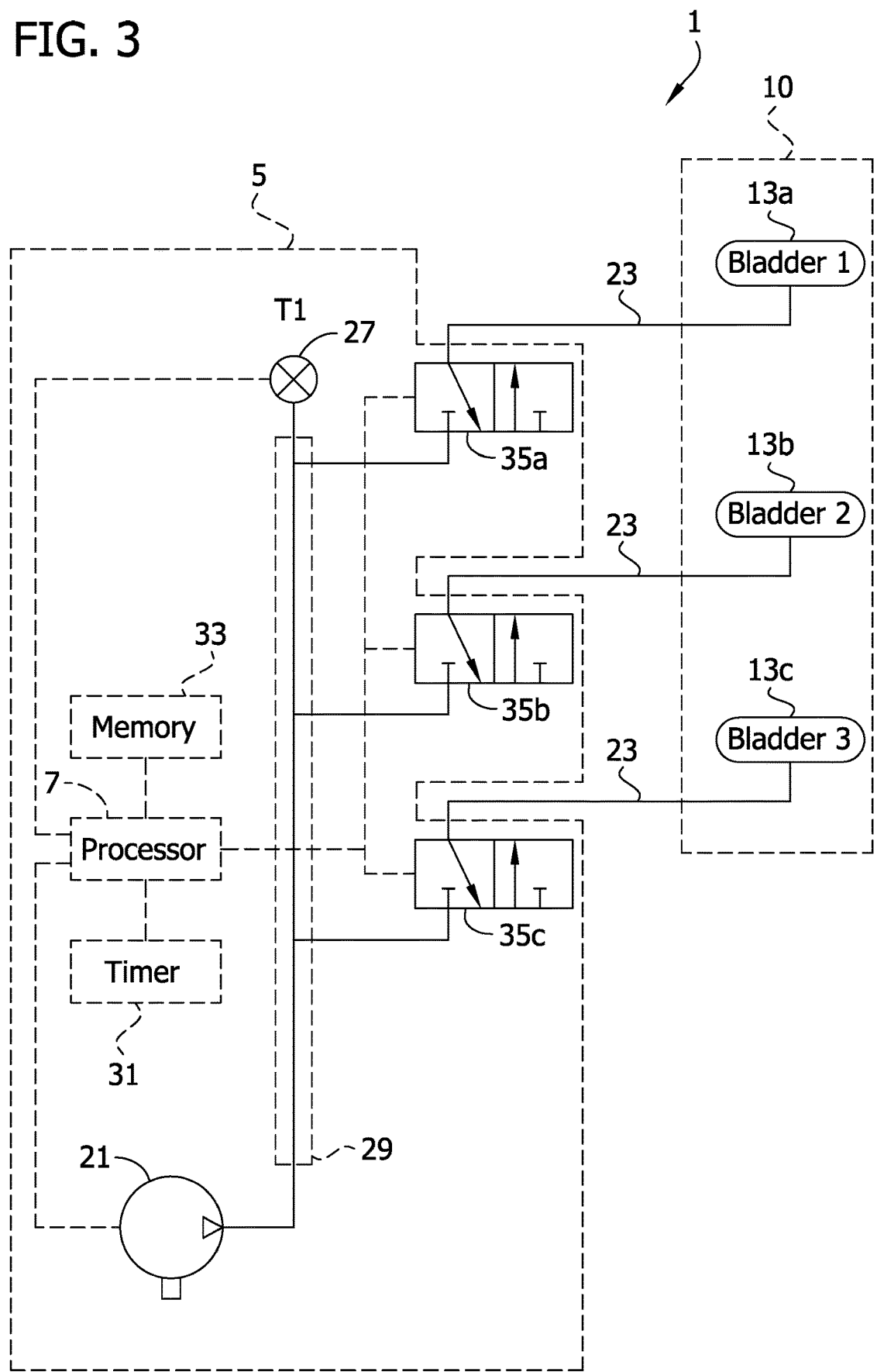
FIG. 3 is a schematic of another exemplary compression system of FIG. 1, including a schematic of a pneumatic circuit.

In an exemplary operation of the embodiment of FIG. 3, in which 3-way/2-position valves are utilized, the computer-executable instructions embodied on the computer readable storage medium 33 include instructions to cause the one or more processors 7 to activate one or more valves 35a, 35b, 35c for one or more of a particular bladder 13a, 13b, 13c such that a fluidic path is established between the pressure sensor 27 and one or more of the bladders 13a, 13b, 13c.

In an exemplary operation of the embodiment of FIG. 2, in which 2-way/2-position valves are utilized, the computer-executable instructions embodied on the computer readable storage medium 33 include instructions to cause the one or more processors 7 to open or close the vent valve 25d such that the manifold 29 can no longer vent. One or more of the computer-executable instructions causes the one or more processors 7 to determine whether the signal received from the pressure sensor 27 includes oscillatory characteristics (e.g., a substantially sinusoidal pattern) indicative of the presence of a heartbeat (i.e., pulse) of the wearer of the compression garment 10. Because a volume of fluid (e.g., air) is retained within one or more of the bladders 13a, 13b, 13c and the manifold 29, a pulse of a wearer of the compression garment can produce a signal with oscillatory characteristics carried on the overall pressure waveform. It should be appreciated that these oscillatory characteristics can be extracted through signal processing of the overall pressure waveform.

Referring to FIG. 4A, a signal from the pressure sensor 27 during a representative bladder inflation period 41 and pressure hold period 43 pressure profile of one of the bladders 13a, 13b, 13c for a wrapped configuration of the compression garment 10 is shown. In this embodiment, the pressure hold period 43 is about twenty seconds in duration and represents one of the bladders 13a, 13b, or 13c inflated to about 200 mmHg. In some embodiments, bladders 13a, 13b, or 13c may be inflated to about 160 mmHg or greater in order to detect wearer blood pressure.

Figure 4B:
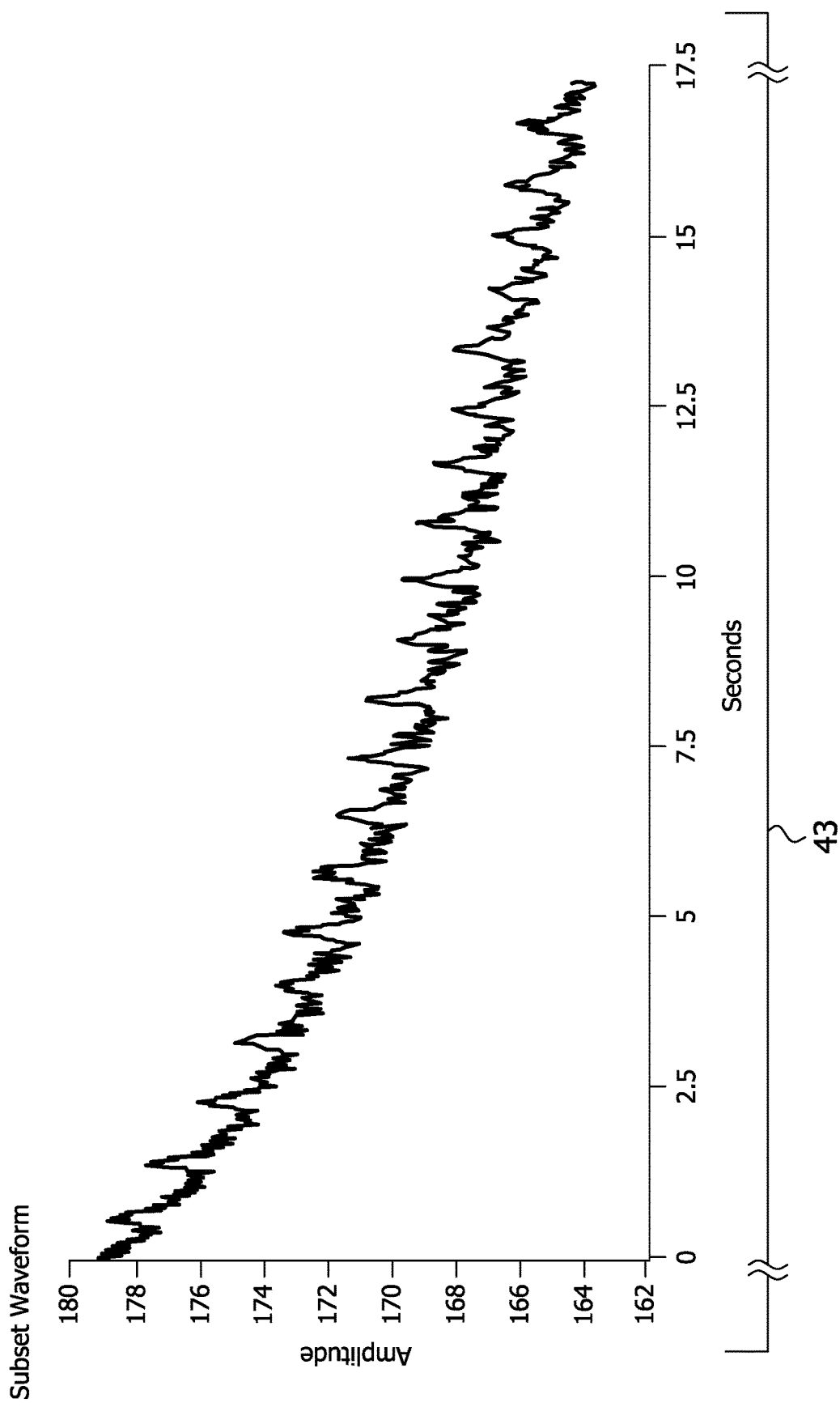

Referring now to FIG. 4B, a representative subset portion of the received pressure signal during pressure hold period 43 is shown. For the sake of explanation herein, the subset portion of the pressure hold period 43 in FIG. 4B is referred to as a subset signal of interest. The computer executable instructions embodied on the non-transitory, computer readable storage medium 33 include instructions to cause the one or more processors 7 to receive signals from the pressure sensor 27 that are indicative of the bladder pressures during the bladder inflation period 41 and the pressure hold period 43. The computer executable instructions can further include instructions to cause the one or more processors 7 to refine the signal from the pressure sensor 27 to extract, from the signal received during the pressure hold period 43, frequencies associated with typical human cardiac cycles. For example, the one or more processors 7 can extract (e.g., through band-pass filtering) frequencies in the range of 0.5 Hz to 25 Hz.

FIG. 4C shows a waveform 43' that is the result of a band-pass filtering technique applied to the signal of interest of the pressure hold period 43 such that the relevant frequency range (e.g., 0.5 Hz to 25 Hz) has been extracted. In some embodiments, the filtered signal 43' brings the oscillations associated with a pulse of a wearer into focus such that the oscillations are more prevalent when displayed by a display device. Additionally or alternatively, the one or more processors 7 filter the signal 43 to remove frequencies that are not associated with a pulse of wearer such that data associated with the resulting filtered signal 43' is further analyzed by the one or more processors 7 as part of peak detection and compliance monitoring algorithms, as described in further detail below. It should be appreciated that, as described herein, the one or more processors 7 detect pulsation associated with the heartbeat of the wearer of the compression garment 10 and not the actual heart rate of the wearer.

Referring to FIG. 4D shows a subset portion of the waveform 43' indicative of the band-pass filtered signal of interest (e.g., an enlarged, fragmentary view of FIG. 4C).

Figure 5:
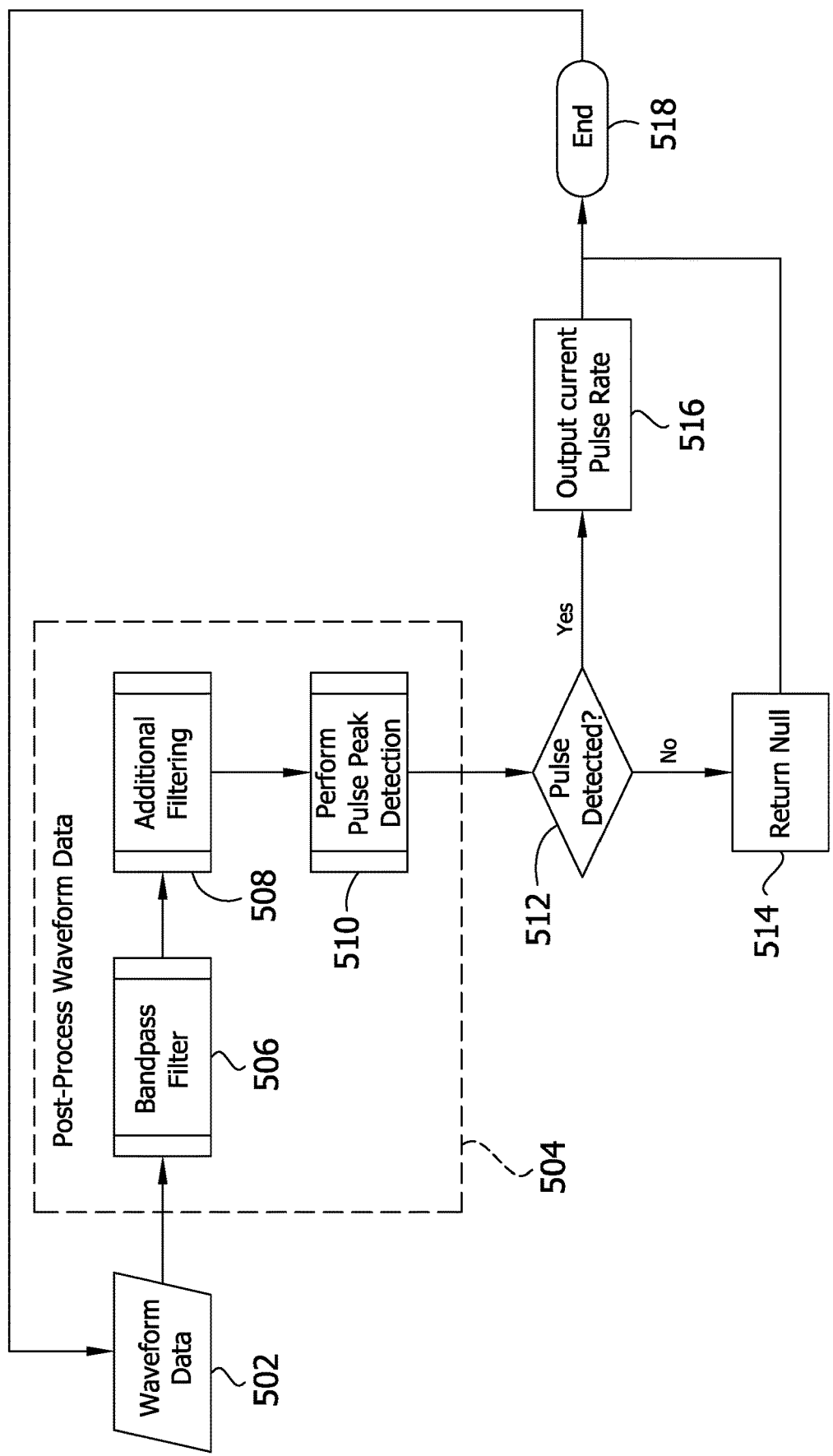
FIG. 5 is a flow diagram of a method of compliance monitoring using the compression system of FIG. 1.

FIG. 5 is a schematic representation of an exemplary method 500 of analyzing waveform data received from the pressure sensor 27 to determine a blood pressure and/or a pulse rate of a wearer around whose limb the compression garment 10 is applied by detecting pulsations associated with the heartbeat of the wearer. This exemplary method can be carried out by the one or more processors 7 through execution of computer executable instructions embodied on the non-transitory, computer readable storage medium 33.

The one or more processors 7 execute computer executable instructions to sample 502 initial pressure. In some embodiments, the initial pressure sampling is done at a rate of 100 Hz or higher and typical signal conditioning is used to remove baseline noise. Additionally or alternatively, the sampling 502 may be expanded to include attenuation of frequencies just under a low cutoff (e.g., 0.25 Hz).

A post-process waveform analysis 504 further includes a bandpass filter 506, an additional filtering 508, and a peak detection 510. During the bandpass filter 506, the signal of interest is filtered using a bandpass filtering technique in a typical range of frequencies associated with a typical heart-rate range of a human wearer (e.g., 0.5-25 Hz for a human wearer).

During the additional filtering 508, the peaks of the bandpass filtered signal are further refined. The additional filtering can include a lowpass filter with a cutoff of 5 Hz to produce a filtered value. Additionally or alternatively, the additional filtering can include a smoothing algorithm using the five most recent samples of the moving range to produce a filtered value. It should be appreciated that more than one filtering technique may be applied to the bandpass filtered signal during the additional filtering step 508.

During a peak detection 510, a peak detection is performed to check that the peaks of the filtered signal correspond to a heartbeat range of a typical human wearer. The peak detection 510 can be based on a predetermined threshold (e.g., look only at peaks with a magnitude greater than 0.05 mmHg). Additionally or alternatively, the peak detection 510 can be based on examining for repeating signals with frequencies within a heartbeat range of a typical human wearer, independent of magnitude (e.g., expanded to 30-120 bpm for margin). For example, a frequency analysis computation may be performed to check that a repeating signal with frequency within the heartbeat range of a typical human wearer is detected. Additionally or alternatively, the peak detection 510 can be based on the highest magnitude peaks and checking that the frequency of those peaks falls within the expected heartbeat range of a typical human wearer. It should be appreciated that more than one peak detection technique may be used during the peak detection 510. In some embodiments, peak detection 510 includes a combination of peak detection based on a predetermined threshold and based on the highest magnitude peaks and checking that the frequency of those peaks falls within the expected heartbeat range of a typical human wearer because the signal-to-noise ratio is high enough that the pulses are plainly evident.

The computer executable instructions cause the one or more processors 7 to determine 512 whether features of a pulse of the wearer were detected during the peak detection 510. If features of a pulse are determined 512 to be present, the results of a positive determination can be indicated 516. For example, the indication 516 can include sending a visual representation to a display device associated with the compression system 1. Additionally or alternatively, the indication 516 can include incrementing and/or pausing a timer (e.g., timer 31). Additionally or alternatively, if features of a pulse are determined 512 to be present, computer executable instructions cause the one or more processors 7 to correlate a determined blood pressure with an arterial blood pressure of the wearer. Upon the indication 516, the process ends at step 518 and returns back to step 502. If an impulse is not detected at step 512, the computer executable instructions cause the one or more processors 7 to return a null value at step 514. After step 514, the process ends at step 518 and returns to sampling 502.

In one aspect, a controller (e.g., controller 5) for controlling inflation and deflation of at least one bladder (e.g., bladders 13a, 13b, 13c) of a garment to provide compression therapy treatment to a wearer of the garment includes one or more processors (e.g., processors 7), and a non-transitory, computer-readable storage medium (e.g., non-transitory computer readable storage medium 33). The non-transitory, computer-readable storage medium includes computer-executable instructions for causing the one or more processors to receive, from a pressure sensor (e.g., pressure sensor 27), a signal indicative of fluid pressure in the at least one bladder of the garment and determine whether the received signal includes oscillating amplitude as a function of time (e.g., timing signals and/or timing data provided by timer 31). The non-transitory, computer-readable storage medium also includes computer-executable instructions for causing the one or more processors to estimate a blood pressure of the wearer of the garment based at least in part on the determination of whether the received signal includes oscillating amplitude as a function of time.

In some embodiments, the instructions to receive the signal indicative of fluid pressure include instructions to receive the signal indicative of fluid pressure while the at least one bladder is inflated.

In certain embodiments, the instructions to receive the signal indicative of fluid pressure include instructions to receive the signal indicative of fluid pressure while the at least one bladder is inflated at a substantially constant pressure.

In some embodiments, the substantially constant pressure changes by less than ten percent over the period of determination.

In certain embodiments, the instructions to receive the signal indicative of fluid pressure include instructions to receive the signal indicative of fluid pressure over a period of greater than about 5 seconds and less than about 60 seconds.

In some embodiments, the instructions to receive the signal indicative of fluid pressure include instructions to receive the signal indicative of fluid pressure at a predetermined interval.

In certain embodiments, the instructions to receive the signal indicative of fluid pressure include instructions to receive the signal between therapeutic compression cycles of the at least one bladder.

In some embodiments, the instructions to receive the signal indicative of fluid pressure include instructions to receive the signal based at least in part on a user input.

In certain embodiments, the non-transitory, computer-readable storage medium further includes computer-executable instructions for causing the one or more processors to detect whether the at least one bladder of the compression garment is in communication with the pressure sensor and the instructions to receive the signal indicative of fluid pressure include instructions to receive the signal based at least in part on detection of the communication between the at least one bladder and the pressure sensor.

In some embodiments, the detected communication between the compression garment and the pressure sensor is fluid communication.

In certain embodiments, the instructions to receive the signal indicative of fluid pressure include instructions to receive the signal indicative of fluid pressure while the at least one bladder is inflated to a non-therapeutic pressure.

In some embodiments, the non-therapeutic pressure is about 160 mmHg or greater.

In certain embodiments, the instructions to receive the signal indicative of fluid pressure include instructions to receive a first signal indicative of fluid pressure in a first bladder and to receive a second signal indicative of fluid pressure in a second bladder, and the instructions to determine whether the received signal includes oscillating amplitude includes instructions to determine whether the first signal and the second signal each include oscillating amplitude.

In some embodiments, the instructions to determine whether the received signal includes oscillating amplitude include instructions to band-pass filter (e.g., bandpass filter 506) the received signal to extract frequencies of about 0.5 Hz to about 25 Hz.

In certain embodiments, the instructions to determine whether the received signal includes oscillating amplitude further include instructions to smooth (e.g., additional filtering 508) the band-pass filtered signal.

In some embodiments, the instructions to determine whether the received signal includes oscillating amplitude further include instructions to low-pass filter (e.g., additional filtering 508) the band-pass filtered signal at a frequency of about 5 Hz or under.

In certain embodiments, the instructions to determine whether the received signal includes oscillating amplitude include instructions to detect peaks (e.g., peak detection 510) in the signal.

In some embodiments, the instructions to detect peaks in the signal include instructions to detect peaks in a frequency range of about 0.5 Hz to about 4 Hz.

In certain embodiments, the instructions to detect peaks in the signal include instructions to detect peaks corresponding to a variation in the fluid pressure of greater than about 0.05 mmHg.

In some embodiments, the instructions to determine whether the received signal includes oscillating amplitude include instructions to detect a repeating signal within a frequency range of about 0.5 Hz to about 4 Hz.

In certain embodiments, the oscillating amplitude as a function of time of the received signal is representative of a pulse of the wearer of the garment.

In some embodiments, the non-transitory, computer-readable storage medium further includes computer-executable instructions for correlating the estimated blood pressure with an arterial blood pressure of the wearer.

In another aspect, a system (e.g., compression system 1) includes a compression garment (e.g., compression garment 10) including at least one inflatable and deflatable bladder (e.g., bladders 13a, 13b, 13c) and the compression garment is securable about one or more limbs of a wearer. The system further includes a controller (e.g., controller 5) for controlling inflation and deflation of at least one bladder of the garment to provide compression therapy treatment to a wearer of the garment. The controller includes one or more processors (e.g., processors 7), and a memory (e.g., non-transitory, computer-readable storage medium 33) that includes instructions for causing the one or more processors to receive, from a pressure sensor (e.g., pressure sensor 27), a signal indicative of fluid pressure in the at least one bladder of the garment and determine whether the received signal includes oscillating amplitude as a function of time (e.g., timing signals and/or timing data provided by timer 31). The non-transitory, computer-readable storage medium also includes computer-executable instructions for causing the one or more processors to estimate the blood pressure of the wearer of the garment based at least in part on the determination of whether the received signal includes oscillating amplitude as a function of time. For example, this can include oscillometric techniques that inflate the bladder to a pressure sufficient to collapse the underlying arterial vessels. In an embodiment, the collapse pressure is referred to as systolic pressure and the pressure which leads to the maximum pulsation amplitude is referred to as the mean arterial pressure. Alternative techniques can leverage pulsewave velocity theory to provide a more continuous blood pressure measurement. For example, the oscillating waveform is first measured in one of the bladders and a second bladder is used to measure the time it takes for the same pressure waveforms to travel along the arterial tree to the second bladder. The less time it takes, the higher the underlying pressure. In yet another embodiment, the inflation profile of a first bladder can be used to generate a measured signal in a second bladder. The known, generated signal can then be used to cancel noise associated with patient motion to improve the fidelity of the underlying blood pressure waveform.

In certain embodiments, the system further includes a pump (e.g., pressurized fluid source 21) and at least one valve (e.g., valves 25a, 25b, 25c) that is in fluid communication with the pump and the at least one inflatable and deflatable bladder. The at least one valve is in electrical communication with the controller and the non-transitory, computer-readable storage medium of the controller also includes computer-executable instructions for causing the one or more processors to actuate the at least one valve to control fluid communication between the pump and the at least one inflatable and deflatable bladder.

In some embodiments, the system also includes a pump in fluid communication with the at least one inflatable and deflatable bladder. The pump is in electrical communication with the controller and the non-transitory, computer-readable storage medium of the controller also includes computer-executable instructions for causing the one or more processors to adjust a speed of the pump.

In certain embodiments, the at least one inflatable and deflatable bladder extends at least partially around a portion (e.g., up to and including a circumference) of the limb of the wearer when secured about the limb of the wearer.

In another aspect, a controller (e.g., controller 5) for controlling inflation and deflation of at least one bladder (e.g., bladders 13a, 13b, 13c) of a garment (e.g., compression garment 10) to provide compression therapy treatment to a wearer of the garment includes one or more processors (e.g., processors 7) and a non-transitory, computer-readable storage medium (e.g., non-transitory computer readable storage medium 33). The non-transitory, computer-readable storage medium includes computer-executable instructions for causing the one or more processors to receive, from a pressure sensor (e.g., pressure sensor 27), a signal indicative of fluid pressure in the at least one bladder of the garment, and determine whether the received signal includes a representation of a pulse of the wearer. The non-transitory, computer-readable storage medium also includes computer-executable instructions for causing the one or more processors to determine a blood pressure of the wearer of the garment based at least in part on the determination of whether the received signal includes a signal indicative of the pulse of the wearer.

In some embodiments, the instructions to receive the signal indicative of fluid pressure include instructions to receive the signal indicative of fluid pressure while the at least one bladder is inflated.

In certain embodiments, the instructions to receive the signal indicative of fluid pressure include instructions to receive the signal indicative of fluid pressure while the at least one bladder is inflated at a substantially constant pressure.

In some embodiments, the instructions to determine whether the received signal includes a representation of a pulse of the wearer include instructions to detect a repeating signal within a frequency range of about 0.5 Hz to about 4 Hz.

In certain embodiments, the computer-executable instructions include instructions for correlating the determined blood pressure with an arterial blood pressure of the wearer.

In another aspect, a system (e.g., compression system 1) includes a compression garment (e.g., compression garment 10) including at least one inflatable and deflatable bladder (e.g., bladders 13a, 13b, 13c) and the compression garment is securable about a limb of a wearer. The system further includes a controller (e.g., controller 5) for controlling inflation and deflation of at least one bladder of the garment to provide compression therapy treatment to the wearer of the garment. The controller includes one or more processors (e.g., processors 7), and a non-transitory, computer-readable storage medium (e.g., non-transitory, computer readable storage medium 33) that includes instructions for causing the one or more processors to receive, from a pressure sensor (e.g., pressure sensor 27), a signal indicative of fluid pressure in the at least one bladder of the garment, and determine whether the received signal includes a representation of a pulse of the wearer. The non-transitory, computer-readable storage medium also includes computer-executable instructions for causing the one or more processors to determine a blood pressure of the wearer of the garment based at least in part on the determination of whether the received signal includes a signal indicative of the pulse of the wearer.

In some embodiments, the system also includes a pump (e.g., pressurized fluid source 21) and at least one valve (e.g., valves 25a, 25b, 25c). The at least one valve is in fluid communication with the pump and the at least one inflatable and deflatable bladder. The at least one valve is also in electrical communication with the controller. The non-transitory, computer-readable storage medium of the controller also includes computer-executable instructions for causing the one or more processors to actuate the at least one valve to control fluid communication between the pump and the at least one inflatable and deflatable bladder.

In certain embodiments, the system also includes a pump in fluid communication with the at least one inflatable and deflatable bladder. The pump is in electrical communication with the controller. The non-transitory, computer-readable storage medium of the controller also includes computer-executable instructions for causing the one or more processors to adjust a speed of the pump.

Embodiments can include one or more of the following advantages.

In some embodiments, a determination of a blood pressure of a wearer is performed using a signal indicative of pressure in an inflatable bladder of the compression garment during a static period, providing a real-time and automated indication of the blood pressure of a wearer. As compared to observations of multiple medical devices made by a caregiver, the real-time and automated indication of blood pressure of the wearer described herein can provide for a more accurate blood pressure measurement, a more accurate indication of patient compliance with treatment protocols, and/or can reduce the burden on the caregiver with respect to monitoring patient vital parameters. As compared to monitoring vital parameters of a wearer who is receiving treatment, the indication of blood pressure of the wearer described herein can provide for monitoring of wearer vital parameters with minimal equipment and enhanced comfort.

While certain embodiments have been described, other embodiments are additionally or alternatively possible.

While compression systems have been described as being used with thigh length compression sleeves, it should be understood that the compression systems can additionally or alternatively be used with other types of compression garments. For example, the compression systems can be used with knee-length compression sleeves and/or with sleeves having a different number of bladders configured to be disposed over different areas of the wearer's body.

Embodiments can be implemented in digital electronic circuitry, or in computer hardware, firmware, software, or in combinations thereof. The controller of the compression system can be implemented in a computer program product tangibly embodied or stored in a machine-readable storage device for execution by a programmable processor; and method actions can be performed by a programmable processor executing a program of instructions to perform functions of the controller of the compression system by operating on input data and generating output. The controller of the compression system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) or FPGAs (field programmable logic arrays).

A number of embodiments have been described. Nevertheless, it will be understood that various modifications may be made without departing from the spirit and scope of the disclosure. For example, while a controller with a single pressure sensor has been described, additional pressure sensors (e.g., one for each inflatable bladder) can be used without departing from the scope of the present disclosure. Accordingly, other embodiments are within the scope of the following claims.

What is claimed is:

1. A controller for controlling inflation and deflation of at least one bladder of a garment to provide compression therapy treatment to a wearer of the garment, and for controlling at least one valve in fluid communication with the inflatable and deflatable bladder, the valve actuatable between a first position in which the inflatable and deflatable bladder is in fluid communication with the atmosphere and a second position in which the inflatable and deflatable bladder is not in fluid communication with the atmosphere, the controller comprising one or more processors and a non-transitory, computer-readable storage medium including computer-executable instructions for causing the one or more processors to:

actuate the valve to the second position to initiate a pressure hold period of a compression therapy cycle;

receive, from a pressure sensor, a signal indicative of fluid pressure in the at least one bladder of the garment during the pressure hold period of the compression therapy cycle when the valve is in the second position;

determine whether the received signal includes oscillating amplitude as a function of time; and based at least in part on the determination of whether the received signal includes oscillating amplitude as a function of time, estimate a blood pressure of the wearer of the garment.

2. The controller of claim 1, wherein the instructions to receive the signal indicative of fluid pressure include instructions to receive the signal indicative of fluid pressure while the at least one bladder is inflated.

3. The controller of claim 2, wherein the instructions to receive the signal indicative of fluid pressure include instructions to receive the signal indicative of fluid pressure while the at least one bladder is inflated at a substantially constant pressure.

4. The controller of claim 1, wherein the instructions to receive the signal indicative of fluid pressure include instructions to receive the signal indicative of fluid pressure at least one of:

at a predetermined interval, and based at least in part on a user input.

5. The controller of claim 1, wherein the instructions to receive the signal indicative of fluid pressure include instructions to receive the signal between therapeutic compression cycles of the at least one bladder.

6. The controller of claim 1, wherein the non-transitory, computer-readable storage medium further includes computer-executable instructions for causing the one or more processors to detect whether the at least one bladder of the compression garment is in fluid communication with the pressure sensor, wherein the instructions to receive the signal indicative of fluid pressure include instructions to receive the signal based at least in part on detection of the fluid communication between the at least one bladder and the pressure sensor.

7. The controller of claim 1, wherein the instructions to receive the signal indicative of fluid pressure include instructions to receive the signal indicative of fluid pressure while the at least one bladder is inflated to a non-therapeutic pressure.

8. The controller of claim 1, wherein the instructions to receive the signal indicative of fluid pressure include instructions to receive a first signal indicative of fluid pressure in a first bladder and to receive a second signal indicative of fluid pressure in a second bladder, and the instructions to determine whether the received signal includes oscillating amplitude includes instructions determine whether the first signal and the second signal each include oscillating amplitude.

9. The controller of claim 1, wherein the instructions to determine whether the received signal includes oscillating amplitude include instructions to band-pass filter the received signal to extract frequencies of 0.5 Hz to 25 Hz.

10. The controller of claim 9, wherein the instructions to determine whether the received signal includes oscillating amplitude further include at least one of: instructions to smooth the band-pass filtered signal; and
instructions to low-pass filter the band-pass filtered signal at a frequency of 5 Hz or under.

11. The controller of claim 1, wherein the instructions to determine whether the received signal includes oscillating amplitude include instructions to detect peaks in the signal.

12. The controller of claim 11, wherein the instructions to detect peaks in the signal include instructions to detect peaks in a frequency range of 0.5 Hz to 4 Hz.

13. The controller of claim 12, wherein the instructions to detect peaks in the signal include instructions to detect peaks corresponding to a variation in the fluid pressure of greater than 0.05 mmHg.

14. The controller of claim 1, wherein the instructions to determine whether the received signal includes oscillating amplitude include instructions to detect a repeating signal within a frequency range of 0.5 Hz to 4 Hz.

15. The controller of claim 1, wherein the oscillating amplitude as a function of time of the received signal is representative of a pulse of the wearer of the garment.

16. The controller of claim 1, wherein the non-transitory, computer-readable storage medium further includes computer-executable instructions for correlating the estimated blood pressure with an arterial blood pressure of the wearer.

17. The controller of claim 1, wherein the non-transitory, computer-readable storage medium further includes computer-executable instructions determining, based at least in part on the received signal indicative of fluid pressure in the at least one bladder of the garment, a respiration rate of the wearer, changes in peripheral resistance, motions of the wearer, or combinations thereof.

18. A system comprising:
a compression garment including:
at least one inflatable and deflatable bladder, the compression garment securable about one or more limbs of a wearer;
a valve in fluid communication with the inflatable and deflatable bladder, the valve actuatable between a first position in which the inflatable and deflatable bladder is in fluid communication with the atmosphere and a second position in which the inflatable and deflatable bladder is not in fluid communication with the atmosphere; and
a controller, the controller comprising a memory and one or more processors, the memory including computer-executable instructions for causing the one or more processors to:
actuate the valve to the second position to initiate a pressure hold period of a compression therapy cycle;
receive, from a pressure sensor, a signal indicative of fluid pressure in the at least one inflatable and deflatable bladder during the pressure hold period of the compression therapy cycle when the valve is in the second position;
determine whether the received signal includes oscillating amplitude as a function of time; and
based at least in part on the determination of whether the received signal includes oscillating amplitude as a function of time, estimate a blood pressure of the wearer.

19. The system of claim 18, further comprising a pump and at least one valve, wherein the at least one valve is in fluid communication with the pump and the at least one inflatable and deflatable bladder, the at least one valve is in electrical communication with the controller, and the memory of the controller further includes computer-executable instructions for causing the one or more processors to actuate the at least one valve to control fluid communication between the pump and the at least one inflatable and deflatable bladder.

20. The system of claim 18, further comprising a pump in fluid communication with the at least one inflatable and deflatable bladder, wherein the pump is in electrical communication with the controller, and the memory of the controller further includes computer-executable instructions for causing the one or more processors to adjust a speed of the pump.

21. The system of claim 18, wherein the at least one inflatable bladder extends at least partially around a portion of the limb of the wearer when secured about the limb of the wearer.

* * * * *